US010842478B2

(12) United States Patent
Hoeppner et al.

(10) Patent No.: US 10,842,478 B2
(45) Date of Patent: Nov. 24, 2020

(54) ANCHORING SYSTEM AND METHOD FOR SECURING A SUTURE TO A PRE-DRILLED BORE

(71) Applicant: Biomet Sports Medicine, LLC, Warsaw, IN (US)

(72) Inventors: Jacy C. Hoeppner, Warsaw, IN (US); Kevin T. Stone, Winona Lake, IN (US); Jason D. Meridew, Warsaw, IN (US); Christopher Palese, South Whitley, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 595 days.

(21) Appl. No.: 15/136,262

(22) Filed: Apr. 22, 2016

(65) Prior Publication Data

US 2016/0310129 A1    Oct. 27, 2016

Related U.S. Application Data

(60) Provisional application No. 62/152,270, filed on Apr. 24, 2015.

(51) Int. Cl.
*A61B 17/04* (2006.01)

(52) U.S. Cl.
CPC ...... *A61B 17/0401* (2013.01); *A61B 17/0483* (2013.01); *A61B 2017/0403* (2013.01);
(Continued)

(58) Field of Classification Search
CPC ............ A61B 17/0401; A61B 17/0483; A61B 2017/0403; A61B 2017/0409;
(Continued)

(56) References Cited

U.S. PATENT DOCUMENTS 6,544,281 B2    4/2003   Elattrache et al.
7,329,272 B2    2/2008   Burkhart et al.
(Continued)

FOREIGN PATENT DOCUMENTS

CN    10298968 A    6/2011
CN    103037814 A    4/2013
(Continued)

OTHER PUBLICATIONS

"International Application Serial No. PCT/US2016/028885, International Preliminary Report on Patentability dated Nov. 2, 2017", 9 pgs.
(Continued)

*Primary Examiner* — Kathleen S Holwerda
*Assistant Examiner* — Brooke Labranche
(74) *Attorney, Agent, or Firm* — Schwegman Lundberg & Woessner, P.A.

(57) ABSTRACT

An anchoring system can use an implant delivery device to deploy an implant into a pre-drilled bore, to secure one or more sutures between a threaded outer surface of an implant body and a wall of the bore. The implant delivery device can controllably rotate the implant about its longitudinal axis. The implant can further include a distal member positioned distal to the implant body and freely rotatable about the longitudinal axis. The implant delivery device can include a finger extending distally from a distal end of an inner shaft. The implant delivery device can controllably translate a wire between a distally extended position, at which the wire can form a closed loop with the finger and a distal end of the inner shaft, and a proximally retracted position, at which the wire can be at least partially retracted into the distal end of the inner shaft.

16 Claims, 6 Drawing Sheets

(52) U.S. Cl.
CPC . *A61B 2017/044* (2013.01); *A61B 2017/0409* (2013.01); *A61B 2017/0414* (2013.01); *A61B 2017/0438* (2013.01); *A61B 2017/0445* (2013.01)

(58) Field of Classification Search
CPC .... A61B 2017/0414; A61B 2017/0438; A61B 2017/044; A61B 2017/0445
See application file for complete search history.

(56) References Cited

U.S. PATENT DOCUMENTS

| | | |
|---|---|---|
| 7,585,311 B2 | 9/2009 | Green et al. |
| 7,993,369 B2 | 8/2011 | Dreyfuss |
| 8,100,942 B1 | 1/2012 | Green et al. |
| 8,109,969 B1 | 2/2012 | Green et al. |
| 8,267,964 B2 | 9/2012 | Green et al. |
| 8,430,909 B2 | 4/2013 | Dreyfuss et al. |
| 9,192,371 B2 | 11/2015 | Palese |
| 2008/0306511 A1 | 12/2008 | Cooper et al. |
| 2009/0264924 A1* | 10/2009 | Ushiba ................ A61B 17/864 606/228 |
| 2009/0281581 A1 | 11/2009 | Berg |
| 2009/0312794 A1 | 12/2009 | Nason et al. |
| 2010/0004683 A1 | 1/2010 | Hoof et al. |
| 2011/0015674 A1* | 1/2011 | Howard ............. A61B 17/0401 606/232 |
| 2011/0015675 A1 | 1/2011 | Howard et al. |
| 2013/0103083 A1 | 4/2013 | Baird |
| 2013/0144334 A1 | 6/2013 | Bouduban et al. |
| 2013/0150885 A1 | 6/2013 | Dreyfuss |
| 2014/0277129 A1 | 9/2014 | Arai et al. |
| 2016/0113643 A1* | 4/2016 | Diduch ............. A61B 17/0401 606/232 |

FOREIGN PATENT DOCUMENTS

| | | |
|---|---|---|
| CN | 103156678 A | 6/2013 |
| CN | 103702619 A | 4/2014 |
| CN | 107809961 | 3/2018 |
| EP | 2218406 A3 | 9/2010 |
| FR | 3005257 | 11/2014 |
| WO | WO-2012129388 A1 | 9/2012 |
| WO | WO-2014177801 A3 | 12/2014 |
| WO | 2016172508 | 10/2016 |

OTHER PUBLICATIONS

"International Application Serial No. PCT/US2016/028885, Written Opinion dated Aug. 8, 2016", 7 pgs.

"International Application Serial No. PCT/US2016/028885, International Search Report dated Aug. 8, 2016", 5 pgs.

"European Application Serial No. 16719727.6, Response filed Jul. 16, 2018 to Office Action dated Jan. 30, 2018", 15 pgs.

"Chinese Application Serial No. 201680031059.4, Office Action dated Oct. 29, 2019", (W/ English Translation), 9 pgs.

"Chinese Application Serial No. 201680031059.4, Response filed Feb. 25, 2020 to Office Action dated Oct. 29, 2019", (W/ English Translation of Claims), 10 pgs.

* cited by examiner

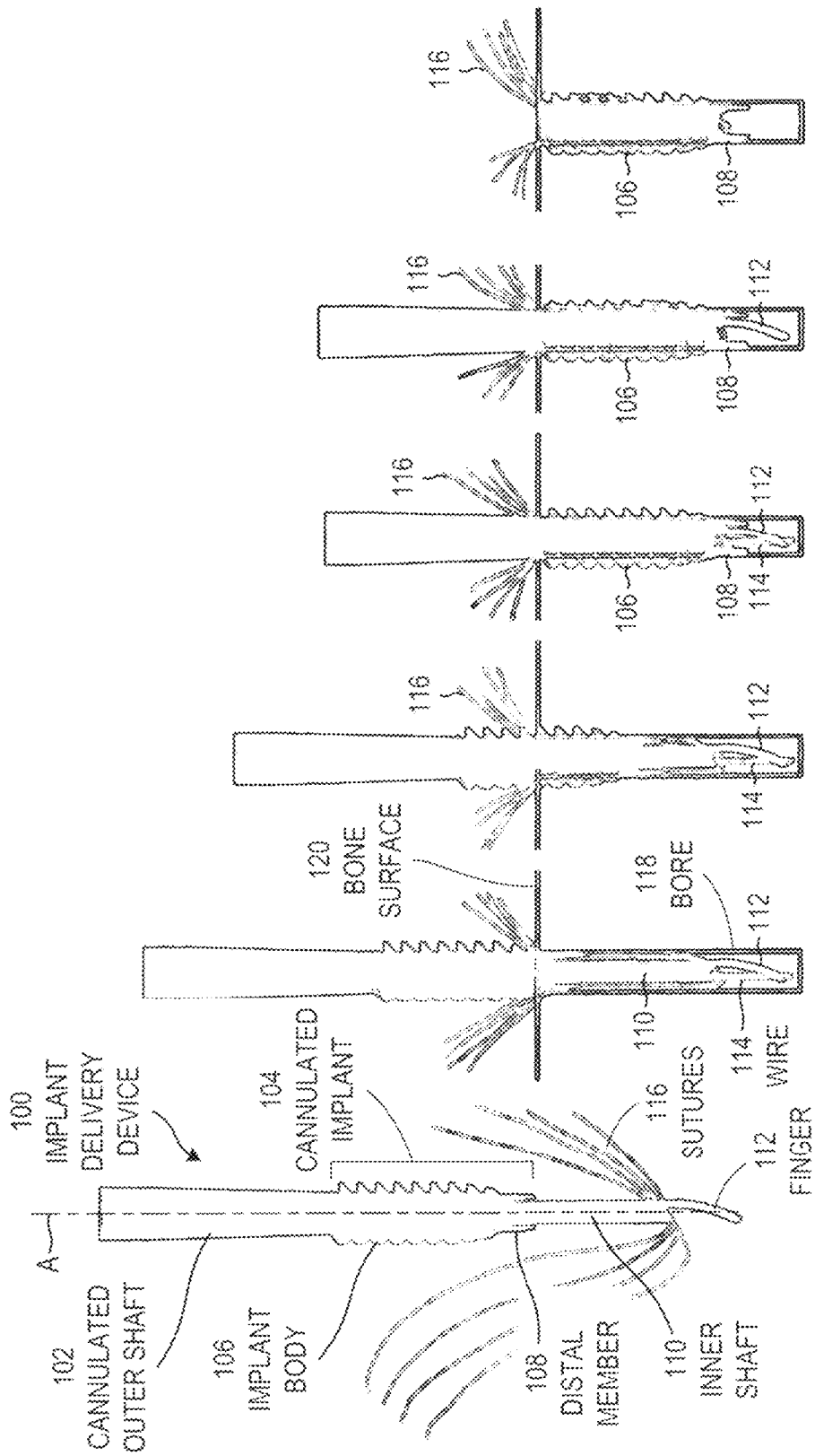

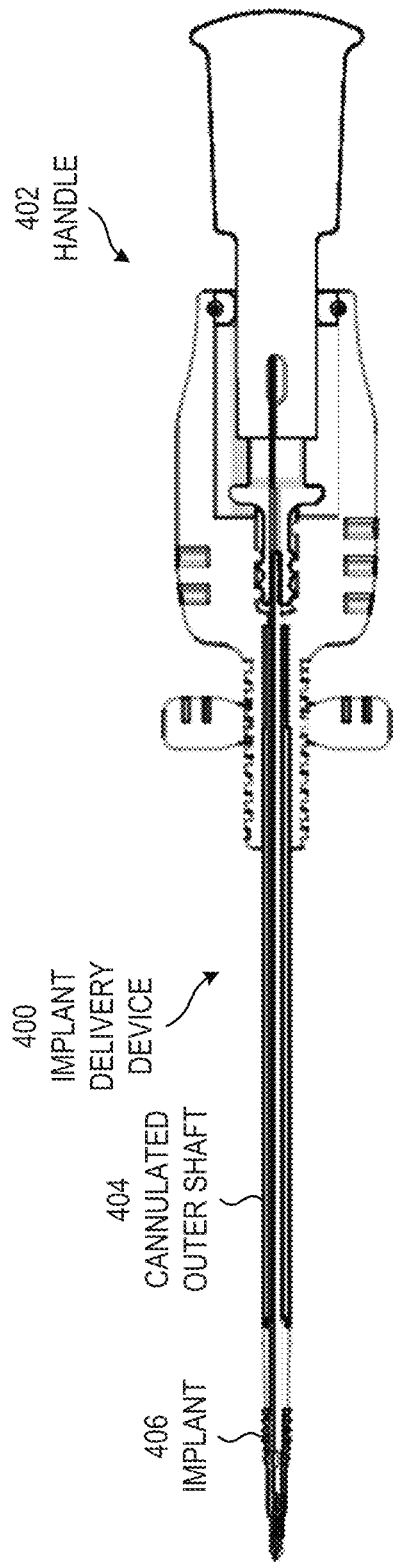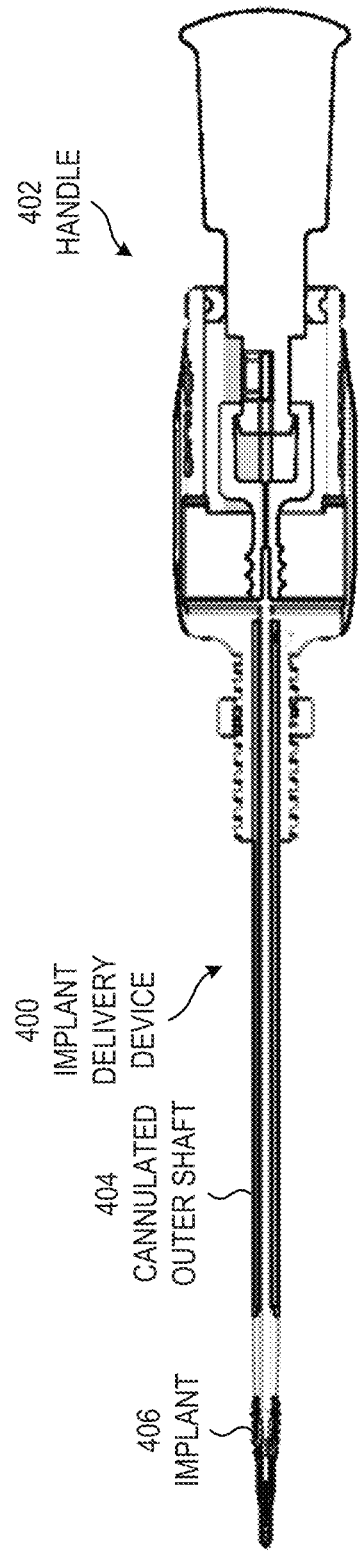
FIG. 4A
FIG. 4B

ANCHORING SYSTEM AND METHOD FOR SECURING A SUTURE TO A PRE-DRILLED BORE

CROSS-REFERENCE TO RELATED APPLICATION

This application claims the benefit of U.S. Provisional Application No. 62/152,270, filed Apr. 24, 2015, which is hereby incorporated by reference in its entirety.

FIELD OF THE DISCLOSURE

The present disclosure relates to securing a suture to a pre-drilled bore, such as in a portion of bone.

BACKGROUND OF THE DISCLOSURE

In the human body, tissue can require repair. For example, a tear in a rotator cuff can require surgical repair of the rotator cuff.

SUMMARY

In a first embodiment, an anchoring system can include a cannulated implant including an implant body and a distal member that is rotatable relative to the implant body about a longitudinal implant axis. The implant body can include a threaded outer surface. The anchoring system can further include an implant delivery device. The implant delivery device can include a cannulated outer shaft extending along a longitudinal delivery device axis. The cannulated outer shaft can include a distal end configured to rotatably engage a proximal end of the implant body for rotating the implant body with the cannulated outer shaft for driving the cannulated implant into bone. The implant delivery device can further include an inner shaft slidably received in the cannulated outer shaft. A distal end of the inner shaft can be extendable distally beyond the distal end of the cannulated outer shaft such that, when the distal end of the cannulated outer shaft is engaging the proximal end of the implant body, the distal end of the inner shaft is extendable through the cannulated implant to a distance beyond the distal member of the cannulated implant. The implant delivery device can further include a finger extending distally beyond the distal end of the inner shaft. The implant delivery device can further include a wire translatable through the inner shaft from a retracted position to an extended position. The extended position can include a distal end of the wire extending a distance beyond the distal end of the inner shaft such that the wire and the finger form at least part of a closed loop for trapping suture.

In a second embodiment, a method for securing a suture to a pre-drilled bore, the method can include: providing an implant delivery device including a distal end, the distal end being convertible from an open configuration to a closed configuration; positioning the distal end of the implant delivery device, in the open configuration, proximate the suture; converting the distal end of the implant delivery device from the open configuration to the closed configuration to encircle the suture in a loop of the closed configuration, the suture being slidable through the loop when the distal end is in the closed configuration; inserting the distal end of the implant delivery device into the pre-drilled bore; deploying a cannulated implant, having a threaded outer surface, from the implant delivery device into the pre-drilled bore, the cannulated implant securing the suture between the threaded outer surface and a wall of the pre-drilled bore when the cannulated implant is deployed; converting the distal end of the implant delivery device from the closed configuration to the open configuration; and retracting the implant delivery device from the pre-drilled bore.

BRIEF DESCRIPTION OF THE DRAWINGS

FIGS. 1A-F show side views of an example of a distal portion of an anchoring system, at sequential stages of operation, in accordance with some embodiments.

FIGS. 4A-B show top and front views of another example of an implant delivery device, including a handle and a cannulated outer shaft, in accordance with some embodiments.

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

Figures 2A, 2B, 2C, 2D, 2E:
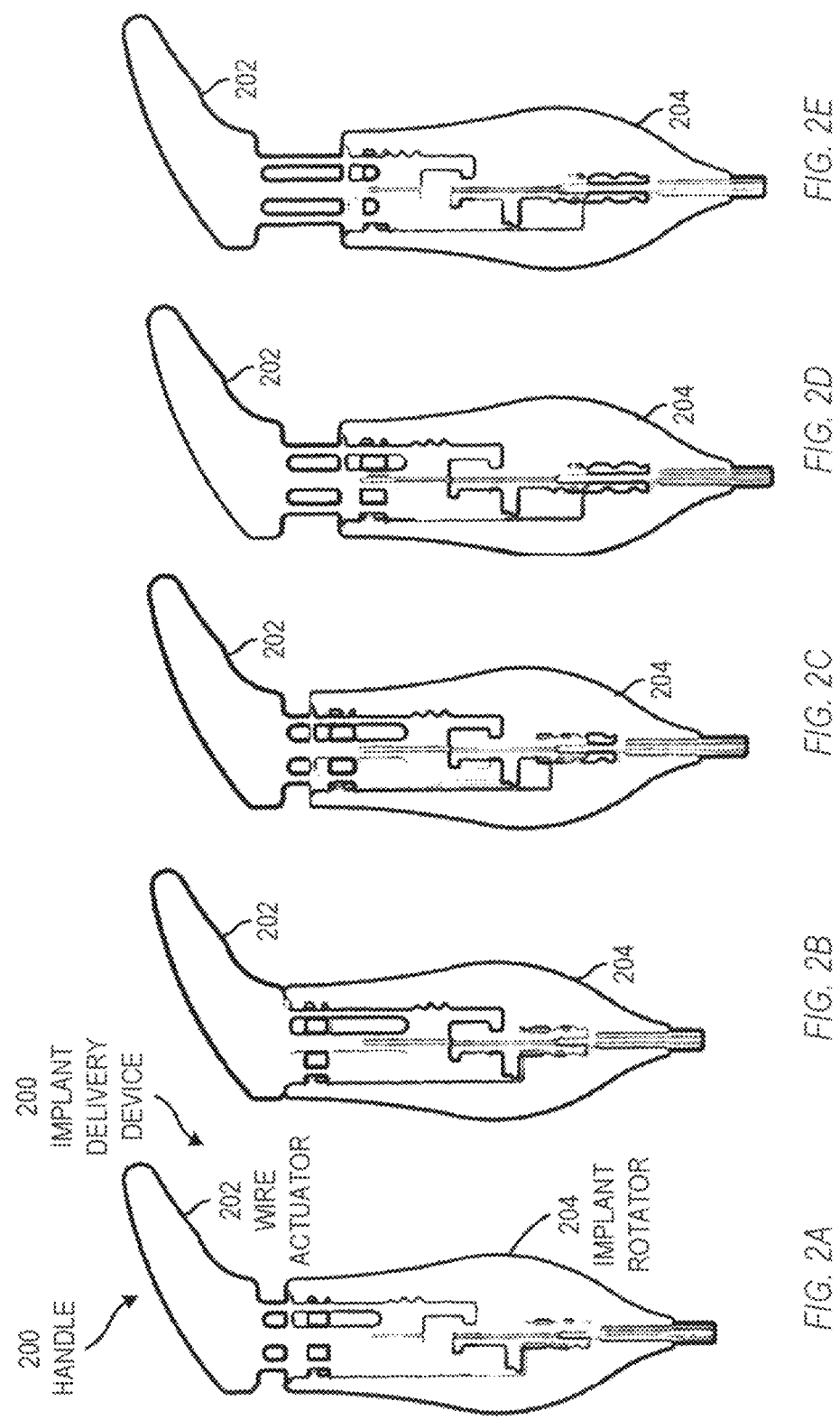
FIGS. 2A-E show side cross-sectional views of an example of a proximal portion of an implant delivery device for securing sutures to a bore in a bone, at sequential stages of operation, in accordance with some embodiments.

During a surgical process, such as a rotator cuff repair surgery, a surgeon can drill one or more bores in a bone. The surgeon can affix sutures to the bone at each bore. For each hole, the surgeon can deploy an implant with an implant body into the bore, which can secure the suture between the threads of the implant body and the wall of the bore. The device and method discussed herein pertain to the implant, the elements used in an implant delivery device that can deploy the implant, and a method of deploying the implant.

An anchoring system can use an implant delivery device to deploy an implant into a pre-drilled bore, to secure one or more sutures between a threaded outer surface of an implant body and a wall of the bore. The implant delivery device can controllably rotate the implant about its longitudinal axis. The implant can further include a distal member positioned distal to the implant body and freely rotatable about the longitudinal axis. The implant delivery device can include a finger extending distally from a distal end of an inner shaft. The implant delivery device can controllably translate a wire between a distally extended position, at which the wire can form a closed loop with the finger and a distal end of the inner shaft, and a proximally retracted position, at which the wire can be at least partially retracted into the distal end of the inner shaft.

FIGS. 1A-F show side views of an example of a distal portion of an anchoring system, at sequential stages of operation, in accordance with some embodiments. The anchoring system can secure at least one suture to a pre-drilled bore. Although the following discussion references "sutures" in the plural form, it should be understood that the anchoring system can also be used to secure a single suture. The anchoring system of FIGS. 1A-F is but one example of an anchoring system; other anchoring systems can also be used.

The anchoring system can include an implant delivery device 100, which can deploy a cannulated implant 104 in a bore 118 to secure sutures 116 at the location of the bore 118. In some examples, the cannulated implant 104 can be pre-loaded onto the implant delivery device 100, and can be shipped with the implant delivery device 100. In other examples, a practitioner can load the cannulated implant 104 onto the implant delivery device 100, as needed. In these examples, the cannulated implant 104 and the sutures 116 are not part of the implant delivery device 100.

The implant delivery device 100 can include a cannulated outer shaft 102 extending along a longitudinal axis (A) of the implant delivery device 100.

The cannulated outer shaft 102 can include at least two concentric elements extending longitudinally from a proximal portion of the cannulated outer shaft 102 to a distal portion of the cannulated outer shaft 102. For example, the cannulated outer shaft 102 can include two or more concentric tubes, or one or more concentric tubes disposed over a wire. One of the concentric elements can be rotated about the longitudinal axis, with respect to another of the concentric elements. When a surgeon initiates a rotation initiated at a handle at a proximal portion of the implant delivery device 100, the concentric elements can couple the rotation to a distal portion of the implant delivery device 100, and can rotate an implant body 106 of a cannulated implant 104 (discussed in detail below).

The cannulated outer shaft 102 can also include two elements that can couple a longitudinal translation with respect to each other from the proximal portion of the cannulated outer shaft 102 to the distal portion of the cannulated outer shaft 102. When a surgeon initiates a translation at the handle at the proximal portion of the implant delivery device 100, the elements can couple the translation to the distal portion of the implant delivery device 100, and can translate a wire 114 (also discussed in detail below).

During a surgical procedure, the implant delivery device 100 can deploy a cannulated implant 104. The cannulated implant 104 remains anchored in the bone after the procedure has been completed, while the implant delivery device 100 is removed. The cannulated implant 104 locks the sutures 116 to the bore by trapping the sutures 116 between external threads on the cannulated implant 104 and a wall of the bore 118. Prior to deployment, the cannulated implant 104 can be disposed over the distal portion of the cannulated outer shaft 102.

The cannulated implant 104 can be disposed over a distal portion of the cannulated outer shaft 102, which can be positioned at a distal portion of the implant delivery device 100.

The cannulated implant 104 can include an implant body 106 having at least one exterior thread and configured to controllably rotate about a longitudinal axis of the implant body 106 (coinciding with A in FIG. 1A). The implant body 106 can include external threads that have an external diameter larger than a diameter of the bore 118. As the surgeon initiates the rotation from the handle, the implant body 106 can rotate around the longitudinal axis, and the threads can screw into the wall of the bore. In some examples, the implant body 106 can slide freely over the distal portion of the cannulated outer shaft 102. In other examples, the implant body 106 can additionally include internal threads having the same pitch as the external threads, so that as the implant body 106 rotates, the implant body moves distally along the cannulated outer shaft 102 at the same rate at which the external threads cut into the wall of the bore 118. Friction between the bone and the implant body 106 can secure the cannulated implant 104 in place in the bore 118 after the surgical procedure has been completed. This friction can, in turn, secure the sutures 116 in place, as well.

The cannulated implant 104 can further including a distal member 108 positioned distal to the implant body 106 and freely rotatable about the longitudinal axis. A distal end of the distal member 108 can include a pair of distal-extending prongs positioned on opposite sides of the longitudinal axis of the implant delivery device 100. As the surgeon rotates the implant body 106, the distal member 108 initially rotates along with the implant body 106. As the implant body 106 moves distally, the distal member 108 eventually contacts the sutures 116. The prongs on the distal member 108 naturally position themselves on opposite sides of the sutures 116 (due to the free rotation), and remain on opposite sides of the sutures 116 as the implant body is 106 is advanced distally to its final position. Once the implant body 106 is advanced fully, the distal member 108 can help prevent the sutures 116 from being pulled proximally as the implant delivery device 100 is removed through a center of the cannulated implant 104.

An inner shaft 110 can extend distally from a distal end of the cannulated outer shaft 110 and can extend at least partially through an interior of the cannulated implant 104.

A finger 112 can extend distally from a distal end of the inner shaft 110. The finger 112 can have a smaller cross-section than the inner shaft 110, when viewed end-on from a distal end of the device 100. The finger 112 can be laterally offset from the longitudinal axis of the implant delivery device 100. In some examples, the finger 112 can curve from a first lateral edge of the inner shaft 110 toward a second lateral edge of the inner shaft 110, opposite the first lateral edge. In some examples, the proximal and distal ends of the finger 112 can be on opposite sides of the longitudinal axis of the implant delivery device 100.

A wire 114 can be controllably translatable between a distally extended position, at which the wire 114 forms a closed loop with the finger 112 and a distal end of the inner shaft 110, and a proximally retracted position, at which the wire 114 is at least partially retracted into the distal end of the inner shaft 110. In some examples, the wire 114 can extend parallel to the finger 112 at a proximal portion of the finger 112. The wire 114 can be shaped so that when the wire is fully extended proximally, the wire 114 can contact a proximal portion of the finger 112, and can form a closed loop from the wire 114, finger 112, and distal end of the inner shaft 110. In some examples, the wire 114 can be formed as a rod, a tube, or other element that can translate longitudinally. In some examples, the wire 114 can optionally include one or more slots, holes, or notches, which can increase the flexibility of the wire 114. The wire 114 can be formed from a metal, plastic, or another suitable material.

A surgeon can open or close the loop from the handle. To do so, the surgeon can impart a longitudinal translation to an element at the handle. The cannulated outer shaft 102 coupled the longitudinal translation from the handle at the proximal portion of the implant delivery device 100, and to the distal portion of the implant delivery device 100, and to the wire 114. The surgeon can retract the wire 114 proximally (thereby opening the loop), or advance the wire 114 distally (thereby closing the loop). The loop can extend over an area, referred to as a window. During a stage of surgery, a surgeon can open the loop (e.g., open the window), position the device 100 so that sutures 116 extend across the finger 112 or distal end of the inner shaft 110 (e.g., the sutures pass through the window), and close the loop. When the loop is closed, the sutures 116 pass through the loop. The surgeon can use this loop to pull the sutures 116 distally to a bottom of the bore 118, then can open the loop and withdraw the inner shaft 110 and finger 112 proximally. The distal member 108 can hold the distalmost portions of the sutures 116 in place when the inner shaft 110 and finger 112 are withdrawn.

Prior to use, the implant delivery device 100 can have its loop either open or closed (e.g., can have the wire 114 retracted proximally or advanced distally). As a first stage during use, the surgeon can position the implant delivery device 100, with the loop open, to "grab" the relevant sutures 116 in the loop. This positioning is performed outside the bone.

In FIG. 1A, the surgeon has grabbed the sutures 116 in the window. At this stage of the surgery, the surgeon has positioned the implant delivery device 100 so that the sutures 116 extend along a distal end of the inner shaft 110 or the finger 112, and the wire 114 is retracted proximally. Next the surgeon manipulates the handle (not shown) of the implant delivery device 100 to distally advance the wire 114 to contact the finger 112, thereby closing the loop. The sutures 116 pass through the closed loop, so that the surgeon can position the sutures 116 by positioning the device 100.

Next, the surgeon can insert a distal end of the implant delivery device 100, with the sutures 116, into the bore 118 in the bone. In FIG. 1B, the surgeon has advanced the implant delivery device 100 distally until the sutures 116 are at or near a bottom of the bore 118, and/or until the implant body 106 contacts a proximal end of the bore 118. With the implant delivery device 100 positioned as in FIG. 1B, the surgeon can adjust the sutures 116 at locations away from the device 100, if needed. For example, if needed, the surgeon can tighten the sutures 116 at respective tissue sites, such as for a rotator cuff under repair.

Next, the surgeon can manipulate the handle (not shown) to rotate the implant body 106 about the longitudinal axis. Such manipulation can distally advance the cannulated implant 104 into the bore 118, as the threads in the implant body 106 engage the wall of the bore 118. The sutures 116 extend distally along one side of the implant body 106 between the threads and the wall of the bore 118, pass through the loop (formed by the wire 114, the finger 112, and the distal end of the bore 118), and extend proximally along an opposite side of the implant body 106 between the threads and the wall of the bore 118. During this advancement of the cannulated implant 104, the inner shaft 110, finger 112, sutures 116, and wire 114 may remain at the same longitudinal position along the bore. In FIG. 1C, the surgeon is halfway through the advancing.

The surgeon can distally advance the cannulated implant 104 into the bore 118 at least until a proximal end of the cannulated implant 104 is flush with a surface 120 of the bone. In FIG. 1D, the surgeon has fully advanced the cannulated implant 104 into the bore 118. At this position, the distal member 108 can be positioned next to the sutures 116, so that the distally-extending prongs on the distal member 108 extend on opposite sides of the sutures 116.

Next, the surgeon can manipulate the handle (not shown) to proximally withdraw the wire 114 into the inner shaft 110, thereby opening the loop. In FIG. 1E, the loop has been opened.

Next, the surgeon can proximally withdraw the implant delivery device 100 (including the cannulated outer shaft 102, the inner shaft 110, the finger 112, and the wire 114) from the bore 118, leaving the cannulated implant 104 (including the implant body 106 and the distal member 108) and the sutures 116 in the bore 118. In FIG. 1F, just the implant body 106, the distal member 108, and the sutures 116 remain in the bore 118. The sutures 116 extend distally along one side of the implant body 106 between the threads and the wall of the bore 118, pass between the distally-extending prongs of the distal member 108, and extend proximally along an opposite side of the implant body 106 between the threads and the wall of the bore 118. The threads form an interference fit that holds the sutures 116 in place. In the stage of FIG. 1F, the cannulated implant 104 is fully implanted.

The elements shown in FIGS. 1A-F can be positioned at a distal end of the implant delivery device 100. At a proximal end of the implant delivery device 100, a handle can control the rotation of the implant body 106 and a proximal/distal position of the wire 114. There are many possible configurations for such a handle. FIGS. 2A-E show one such configuration.

FIGS. 2A-E show side cross-sectional views of an example of a proximal portion of an implant delivery device 100 for securing sutures to a bore 118 in a bone, at sequential stages of operation, in accordance with some embodiments. The configuration of FIGS. 2A-E is but one example; other suitable configurations can also be used.

In the example of FIGS. 2A-E, the implant delivery device 100 can include a handle 200 at a proximal end of the implant delivery device 100. The handle 200 can include a wire actuator 202 at a proximal end of the handle 200, and an implant rotator 204 distal to the wire actuator 202. By translating the wire actuator 202 proximally or distally with respect to the implant rotator 204, a surgeon can proximally retract or distally advance the wire 114 with respect to the inner shaft 110 (FIG. 1B). By rotating the implant rotator 204 with respect to the wire actuator 202, the surgeon can rotate the implant body 106 around the longitudinal axis.

In FIG. 2A, the wire actuator 202 has been pulled proximally from the implant rotator 204, so that the wire 114 is proximally retracted in the inner shaft 110. The loop is open. The state of the handle 200 in FIG. 2A corresponds to the state of the device 100 in FIG. 1A.

In FIG. 2B, the wire actuator 202 has been pushed distally toward the implant rotator 204, so that the wire 114 is distally advanced toward the finger 112. The loop is closed. The state of the handle 200 in FIG. 2B corresponds to the state of the device 100 in FIG. 1B.

In FIG. 2C, the implant rotator 204 has been rotated with respect to the wire actuator 202, to roughly half its range of travel. The loop is closed. The state of the handle 200 in FIG. 2C corresponds to the state of the device 100 in FIG. 1C.

In FIG. 2D, the implant rotator 204 has been rotated with respect to the wire actuator 202, to the end of its range of travel. The loop is closed. The state of the handle 200 in FIG. 2D corresponds to the state of the device 100 in FIG. 1D.

In FIG. 2E, the wire actuator 202 has been pulled proximally from the implant rotator 204, so that the wire 114 is proximally retracted in the inner shaft 110. The loop is open. The state of the handle 200 in FIG. 2E corresponds to the state of the device 100 in FIG. 1E.

It will be understood that that handle configuration and the actuator configurations of FIGS. 2A-2E are but examples, and that other suitable configurations can be used for the handle and actuators. FIGS. 3-5 show examples of such other suitable configurations.

Figure 3A:
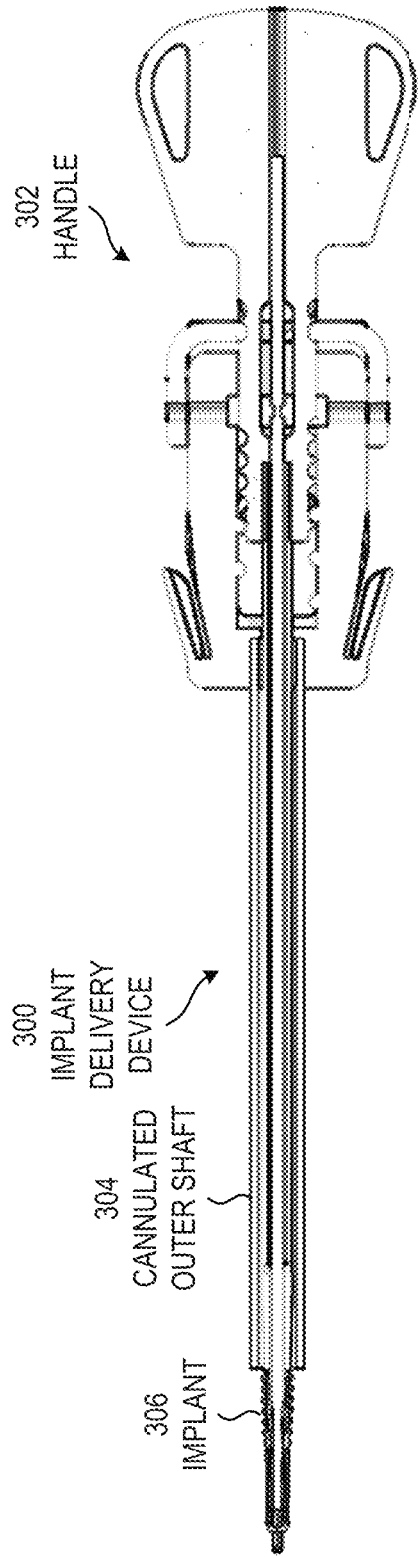
FIGS. 3A-B show top and front views of an example of an implant delivery device, including a handle and a cannulated outer shaft, in accordance with some embodiments.
Figure 3B:
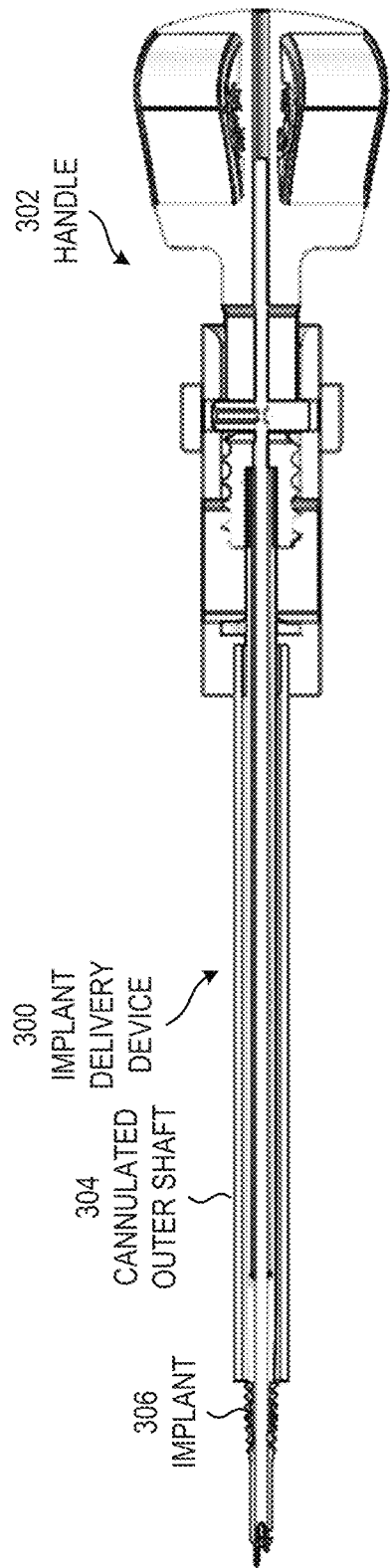

FIGS. 3A-B show top and front views of an example of an implant delivery device 300, including a handle 302 and a cannulated outer shaft 304, in accordance with some embodiments. An implant 306 is configured to be deployed by the implant delivery device 300.

FIGS. 4A-B show top and front views of another example of an implant delivery device 400, including a handle 402 and a cannulated outer shaft 404, in accordance with some embodiments. An implant 406 is configured to be deployed by the implant delivery device 400.

Figure 5A:
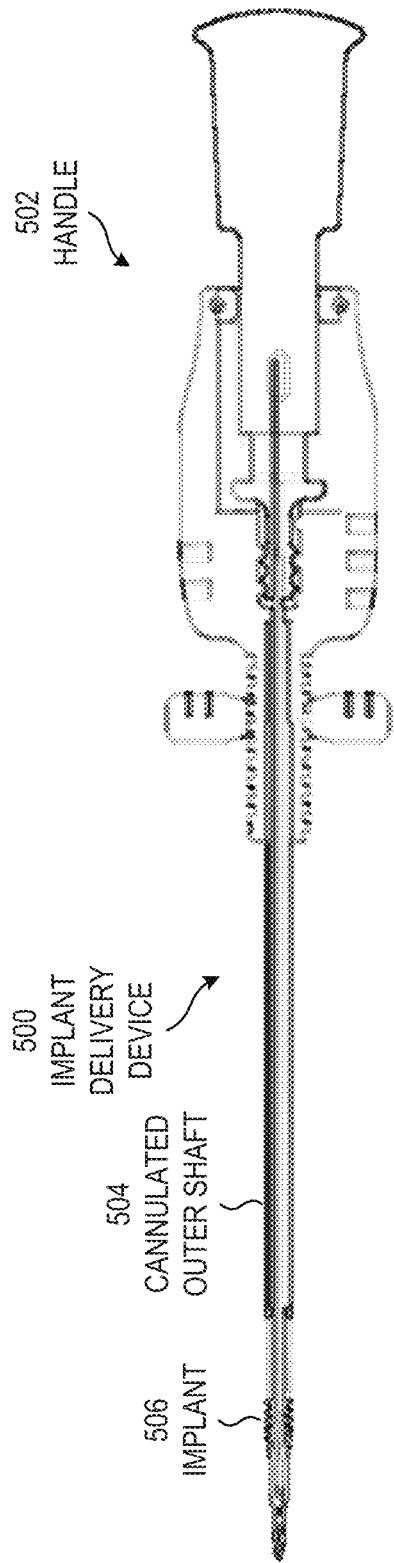
FIGS. 5A-B show top and front views of still another example of an implant delivery device, including a handle and a cannulated outer shaft, in accordance with some embodiments.
Figure 5B:
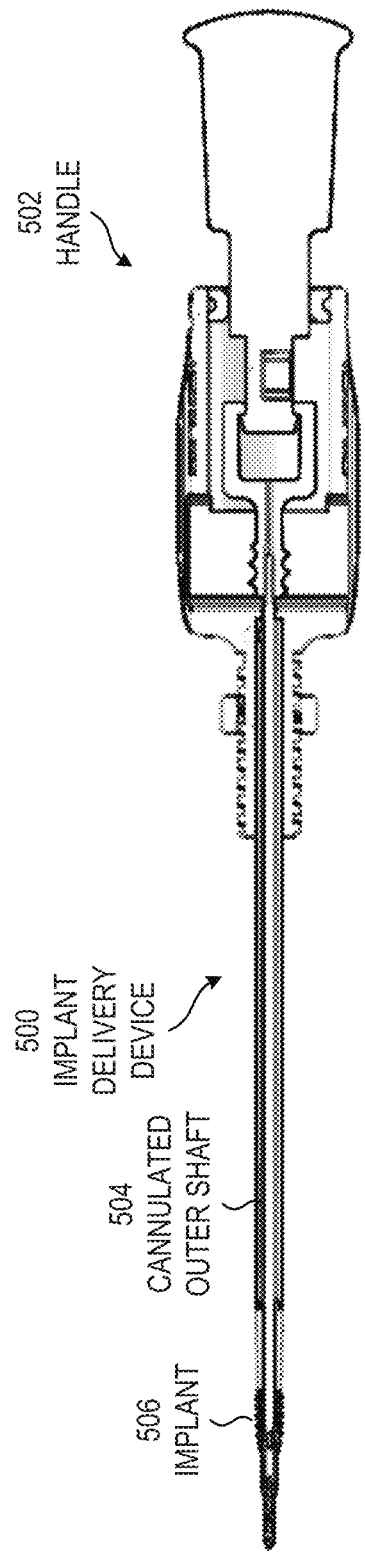

FIGS. 5A-B show top and front views of still another example of an implant delivery device 500, including a handle 502 and a cannulated outer shaft 504, in accordance with some embodiments. An implant 506 is configured to be deployed by the implant delivery device 500.

The configurations of FIGS. 3-5 are but examples of implant delivery devices. In each configuration, and others not shown, the handles can include suitable mechanisms to deploy the implant, including a mechanism configured to transmit torque or rotation to the implant, and a mechanism configured to transmit longitudinal translation to the wire.

Figure 6:
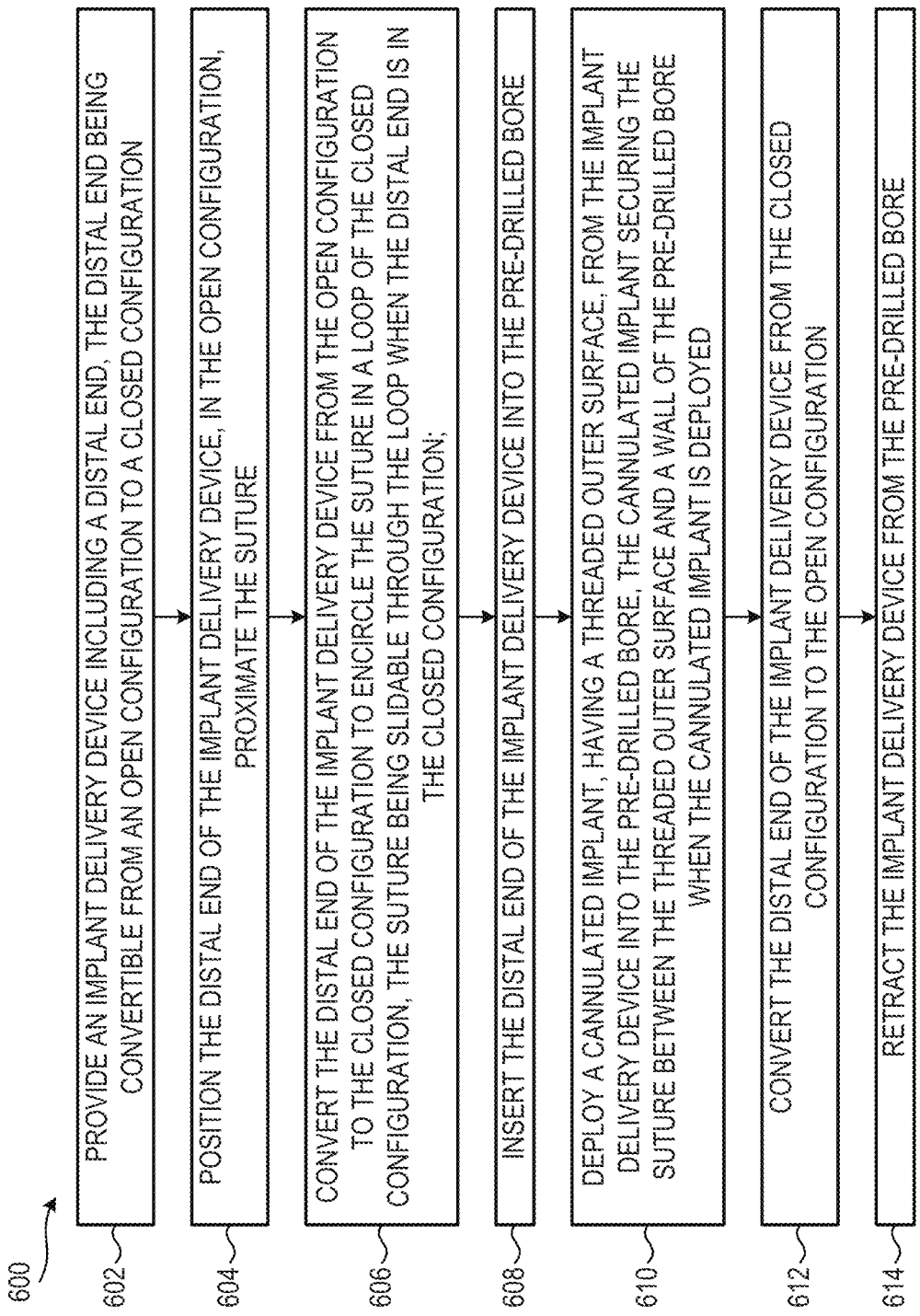
FIG. 6 shows a flow chart of an example of a method for securing a suture to a pre-drilled bore, in accordance with some embodiments.

FIG. 6 shows a flow chart of an example of a method 600 for securing a suture to a pre-drilled bore, in accordance with some embodiments. The method 600 can be executed by a surgeon using an anchoring system, such as the anchoring system shown in FIGS. 1-5, or others. The method 600 is but one example for securing a suture to a pre-drilled bore; other suitable methods can also be used.

At operation 602, the surgeon can provide an implant delivery device including a distal end, the distal end being convertible from an open configuration to a closed configuration.

At operation 604, the surgeon can position the distal end of the implant delivery device, in the open configuration, proximate the suture.

At operation 606, the surgeon can convert the distal end of the implant delivery device from the open configuration to the closed configuration to encircle the suture in a loop of the closed configuration, the suture being slidable through the loop when the distal end is in the closed configuration.

At operation 608, the surgeon can insert the distal end of the implant delivery device into the pre-drilled bore.

At operation 610, the surgeon can deploy a cannulated implant, having a threaded outer surface, from the implant delivery device into the pre-drilled bore, the cannulated implant securing the suture between the threaded outer surface and a wall of the pre-drilled bore when the cannulated implant is deployed.

At operation 612, the surgeon can convert the distal end of the implant delivery device from the closed configuration to the open configuration.

At operation 614, the surgeon can retract the implant delivery device from the pre-drilled bore.

In some examples, the implant delivery device can further include two concentric elements extending along a longitudinal axis of the implant delivery device from a proximal portion of the implant delivery device to a distal portion of the implant delivery device. In these examples, controllably rotating the implant body about the longitudinal axis of the implant delivery device can include at the proximal portion of the implant delivery device, imparting a rotation to one of the concentric elements with respect to the other of the concentric elements; and coupling the rotation from proximal portions of the concentric elements to distal portions of the concentric elements; and coupling the rotation from the distal portions of the concentric elements to the implant body. In some examples, the two concentric elements are the cannulated outer shaft and the inner shaft.

To further illustrate the device and related method disclosed herein, a non-limiting list of examples is provided below. Each of the following non-limiting examples can stand on its own, or can be combined in any permutation or combination with any one or more of the other examples.

In Example 1, an anchoring system comprises a cannulated implant including an implant body and a distal member that is rotatable relative to the implant body about a longitudinal implant axis, the implant body including a threaded outer surface; and an implant delivery device, comprising: a cannulated outer shaft extending along a longitudinal delivery device axis, the cannulated outer shaft including a distal end configured to rotatably engage a proximal end of the implant body for rotating the implant body with the cannulated outer shaft for driving the cannulated implant into bone; an inner shaft slidably received in the cannulated outer shaft, wherein a distal end of the inner shaft is extendable distally beyond the distal end of the cannulated outer shaft such that, when the distal end of the cannulated outer shaft is engaging the proximal end of the implant body, the distal end of the inner shaft is extendable through the cannulated implant to a distance beyond the distal member of the cannulated implant; a finger extending distally beyond the distal end of the inner shaft; and a wire translatable through the inner shaft from a retracted position to an extended position, the extended position including a distal end of the wire extending a distance beyond the distal end of the inner shaft such that the wire and the finger form at least part of a closed loop for trapping suture.

In Example 2, the device of Example 1 can optionally be configured such that the finger has a smaller cross-section than the inner shaft, when viewed end-on from a distal end of the implant delivery device.

In Example 3, the device of any one or a combination of Examples 1-2 can optionally be configured such that the finger is laterally offset from the longitudinal delivery device axis.

In Example 4, the device of any one or a combination of Examples 1-3 can optionally be configured such that the finger curves from a first lateral edge of the inner shaft toward a second lateral edge of the inner shaft, opposite the first lateral edge.

In Example 5, the device of any one or a combination of Examples 1-4 can optionally be configured such that a proximal end of the finger and a distal end of the finger are disposed on opposite sides of the longitudinal delivery device axis.

In Example 6, the device of any one or a combination of Examples 1-5 can optionally be configured such that the wire extends parallel to the finger at a proximal portion of the finger.

In Example 7, the device of any one or a combination of Examples 1-6 can optionally be configured such that the wire is shaped so that when the wire is in the extended position, the wire contacts a distal portion of the finger.

In Example 8, the device of any one or a combination of Examples 1-7 can optionally be configured such that the distal member includes include a pair of distally-extending prongs positioned on opposite sides of the longitudinal implant axis.

In Example 9, the device of any one or a combination of Examples 1-8 can optionally be configured such that the distal member is configured so that as the cannulated implant is advanced distally to a first position at which the prongs and trapped suture are at the same longitudinal location, the distal member is able to freely rotate to position the prongs on opposite sides of the trapped suture.

In Example 10, the device of any one or a combination of Examples 1-9 can optionally be configured such that as the cannulated implant is advanced distally beyond the first position, the prongs are able to remain on opposite sides of the trapped suture.

In Example 11, the device of any one or a combination of Examples 1-10 can optionally be configured such that a proximal portion of the implant delivery device is coupled to a handle; the handle includes a wire actuator configured to controllably translate the wire; and the handle includes an implant actuator configured to controllably rotate the cannulated implant about the longitudinal implant axis.

In Example 12, the device of any one or a combination of Examples 1-11 can optionally be configured such that the implant actuator is configured to controllably rotate the cannulated outer shaft about the longitudinal delivery device axis and thereby controllably rotate the cannulated implant about the longitudinal implant axis.

In Example 13, the device of any one or a combination of Examples 1-12 can optionally be configured such that the threaded outer surface is configured to cut into a wall of a pre-drilled bore as the cannulated implant is rotated about the longitudinal implant axis; and the implant body further includes a threaded inner surface, the threaded inner surface having a pitch matched to a pitch of the threaded outer surface, so that as the cannulated implant is rotated about the longitudinal implant axis, the cannulated implant is able to move distally along the inner shaft at the same rate at which the threaded outer surface cuts into the wall of the pre-drilled bore.

In Example 14, the device of any one or a combination of Examples 1-13 can optionally be configured such that when the wire is in the extended position, the wire and the finger form a fully closed loop for trapping the suture.

In Example 15, the device of any one or a combination of Examples 1-14 can optionally be configured such that when the wire is in the extended position, the wire, the finger, and the distal end of the inner shaft form a fully closed loop for trapping the suture.

In Example 16, a method for securing a suture to a pre-drilled bore comprises: providing an implant delivery device including a distal end, the distal end being convertible from an open configuration to a closed configuration; positioning the distal end of the implant delivery device, in the open configuration, proximate the suture; converting the distal end of the implant delivery device from the open configuration to the closed configuration to encircle the suture in a loop of the closed configuration, the suture being slidable through the loop when the distal end is in the closed configuration; inserting the distal end of the implant delivery device into the pre-drilled bore; deploying a cannulated implant, having a threaded outer surface, from the implant delivery device into the pre-drilled bore, the cannulated implant securing the suture between the threaded outer surface and a wall of the pre-drilled bore when the cannulated implant is deployed; converting the distal end of the implant delivery device from the closed configuration to the open configuration; and retracting the implant delivery device from the pre-drilled bore.

In Example 17, the method of Example 16 can optionally be configured such that deploying the cannulated implant comprises: controllably rotating the cannulated implant about a longitudinal implant axis of the cannulated implant.

In Example 18, the method of any one or a combination of Examples 16-17 can optionally be configured such that controllably rotating the cannulated implant about a longitudinal implant axis of the cannulated implant comprises: at a proximal portion of the implant delivery device, imparting a rotation to a cannulated outer shaft of the implant delivery device; and rotatably coupling a distal end of the cannulated outer shaft to a proximal end of the cannulated implant.

In Example 19, the method of any one or a combination of Examples 16-18 can optionally be configured such that converting the distal end of the implant delivery device from the open configuration to the closed configuration comprises: controllably advancing a portion of a wire from within an inner shaft of the implant delivery device to contact a distally-extending finger at the distal end of the implant delivery device.

In Example 20, the method of any one or a combination of Examples 16-19 can optionally be configured such that converting the distal end of the implant delivery device from the closed configuration to the open configuration comprises: controllably retracting the portion of the wire into the inner shaft.

While this invention has been described as having example designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An anchoring system, comprising: a suture; a cannulated implant including an implant body and a distal member that is rotatable relative to the implant body about a longitudinal implant axis, the implant body including a threaded outer surface; and an implant delivery device, comprising: a cannulated outer shaft extending along a longitudinal delivery device axis, the cannulated outer shaft including a distal end configured to rotatably engage a proximal end of the implant body for rotating the implant body with the cannulated outer shaft for driving the cannulated implant into bone; an inner shaft slidably received in the cannulated outer shaft, wherein a distal end of the inner shaft is extendable distally beyond the distal end of the cannulated outer shaft such that, when the distal end of the cannulated outer shaft is engaging the proximal end of the implant body, the distal end of the inner shaft is extendable through the cannulated implant to a distance beyond the distal member of the cannulated implant, wherein the inner shaft is attached directly to a finger that extends distally from the distal end of the inner shaft; a wire comprising a rod or tube translatable through the inner shaft from a retracted position to an extended position, the extended position including a distal end of the wire extending distally beyond the distal end of the inner shaft and the distal member of the cannulated implant such that the wire and the finger together form at least part of a closed loop for trapping the suture at the distance beyond the distal member of the cannulated implant, wherein the wire and the finger are configured to form the at least part of the closed loop for trapping the suture prior to and upon insertion of the inner shaft, the finger and the wire into a pre-drilled bore in a bone of a patient, wherein the pre-drilled bore is sized and shaped to receive the cannulated implant when rotatably driven by the outer shaft.

2. The anchoring system of claim 1, wherein the finger has a smaller cross-section than the inner shaft, when viewed end-on from a distal end of the implant delivery device.

3. The anchoring system of claim 1, wherein the finger is laterally offset from the longitudinal delivery device axis.

4. The anchoring system of claim 1, wherein the finger curves from a first lateral edge of the inner shaft toward a second lateral edge of the inner shaft, opposite the first lateral edge.

5. The anchoring system of claim 4, wherein a proximal end of the finger and a distal end of the finger are disposed on opposite sides of the longitudinal delivery device axis.

6. The anchoring system of claim 1, wherein the wire extends parallel to finger at a proximal portion of the finger.

7. The anchoring system of claim 1, wherein the wire is shaped so that when the wire is in the extended position, the wire contacts a distal portion of the finger.

8. The anchoring system of claim 1, wherein the distal member includes a pair of distally-extending prongs positioned on opposite sides of the longitudinal implant axis.

9. The anchoring system of claim 8, wherein the distal member is configured so that as the cannulated implant is advanced distally to a first position at which the prongs and trapped suture are at the same longitudinal location, the distal member is able to freely rotate to position the prongs on opposite sides of the trapped suture.

10. The anchoring system of claim 9, wherein as the cannulated implant is advanced distally beyond the first position, the prongs are able to remain on opposite sides of the trapped suture.

11. The anchoring system of claim 1, wherein:
a proximal portion of the implant delivery device is coupled to a handle;
the handle includes a wire actuator configured to controllably translate the wire; and
the handle includes an implant actuator configured to controllably rotate the cannulated implant about the longitudinal implant axis.

12. The anchoring system of claim 11, wherein the implant actuator is configured to controllably rotate the cannulated outer shaft about the longitudinal delivery device axis and thereby controllably rotate the cannulated implant about the longitudinal implant axis.

13. The anchoring system of claim 12, wherein: the threaded outer surface is configured to cut into a wall of the pre-drilled bore as the cannulated implant is rotated about the longitudinal implant axis; and the implant body further includes a threaded inner surface, the threaded inner surface having a pitch matched to a pitch of the threaded outer surface, so that as the cannulated implant is rotated about the longitudinal implant axis, the cannulated implant is able to move distally along the inner shaft at the same rate at which the threaded outer surface cuts into the wall of the pre-drilled bore.

14. The anchoring system of claim 1, wherein when the wire is in the extended position, the wire and the finger form a fully closed loop for trapping the suture.

15. The anchoring system of claim 1, wherein when the wire is in the extended position, the wire, the finger, and the distal end of the inner shaft form a fully closed loop for trapping the suture.

16. An anchoring system, comprising: a suture; a cannulated implant including an implant body and a distal member that is rotatable relative to the implant body about a longitudinal implant axis; and an implant delivery device, comprising: a cannulated outer shaft extending along a longitudinal delivery device axis, the cannulated outer shaft including a distal end configured to rotatably engage a proximal end of the implant body for rotating the implant body with the cannulated outer shaft for driving the cannulated implant into bone; an inner shaft received in the cannulated outer shaft and moveable relative thereto, wherein a distal end of the inner shaft is extendable distally beyond the distal end of the cannulated outer shaft, wherein the inner shaft is attached directly to a finger that extends distally from the distal end of the inner shaft; and a wire translatable through the inner shaft from a retracted position to an extended position, the extended position including a distal end of the wire extending a distance beyond the distal end of the inner shaft; wherein the finger is laterally offset from the longitudinal delivery device axis, wherein the finger curves from a first lateral edge of the inner shaft toward a second lateral edge of the inner shaft, opposite the first lateral edge, and wherein a proximal end of the finger and a distal end of the finger are disposed on opposite sides of the longitudinal delivery device axis; wherein the wire is shaped so that when the wire is in the extended position, the wire contacts a distal portion of the finger whereby the wire and the finger form at least part of a closed loop to trap the suture distal of the implant body.

\* \* \* \* \*

UNITED STATES PATENT AND TRADEMARK OFFICE
CERTIFICATE OF CORRECTION

| | | |
|---|---|---|
| PATENT NO. | : 10,842,478 B2 | Page 1 of 1 |
| APPLICATION NO. | : 15/136262 | |
| DATED | : November 24, 2020 | |
| INVENTOR(S) | : Hoeppner et al. | |

It is certified that error appears in the above-identified patent and that said Letters Patent is hereby corrected as shown below:

In the Claims

In Column 11, Line 18, in Claim 6, after "to", insert --the--

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*